United States Patent
Kost et al.

(10) Patent No.: US 10,960,233 B2
(45) Date of Patent: Mar. 30, 2021

(54) LOW INTENSITY ULTRASOUND THERAPY

(71) Applicant: B.G. NEGEV TECHNOLOGIES AND APPLICATIONS LTD., Beer Sheva (IL)

(72) Inventors: Joseph Kost, Omer (IL); Aharon Azaguri, Kiryat Gat (IL); Yana Yudilevich, Beer Sheva (IL)

(73) Assignee: B.G. NEGEV TECHNOLOGIES AND APPLICATIONS LTD., Beer Sheva (IL)

( * ) Notice: Subject to any disclaimer, the term of this patent is extended or adjusted under 35 U.S.C. 154(b) by 56 days.

(21) Appl. No.: 14/198,701

(22) Filed: Mar. 6, 2014

(65) Prior Publication Data
US 2014/0257146 A1  Sep. 11, 2014

Related U.S. Application Data

(60) Provisional application No. 61/773,169, filed on Mar. 6, 2013.

(51) Int. Cl.
*A61N 7/00*  (2006.01)

(52) U.S. Cl.
CPC ........ *A61N 7/00* (2013.01); *A61N 2007/0004* (2013.01)

(58) Field of Classification Search
CPC .............. A61N 7/00; A61N 2007/0004; A61H 23/0245
See application file for complete search history.

(56) References Cited

U.S. PATENT DOCUMENTS

| | | | |
|---|---|---|---|
| 6,589,173 B1* | 7/2003 | Mitragotri | A61B 8/00 600/437 |
| 7,481,781 B2 | 1/2009 | Craig et al. | |
| 2002/0004052 A1* | 1/2002 | Berd et al. | 424/277.1 |
| 2005/0054958 A1* | 3/2005 | Hoffmann | A61B 17/225 601/46 |
| 2007/0088345 A1* | 4/2007 | Larson et al. | 606/27 |
| 2008/0056937 A1* | 3/2008 | Cordemans De Meulenaer et al. | 422/20 |
| 2008/0071312 A1* | 3/2008 | Ridgway | 607/1 |
| 2010/0092424 A1* | 4/2010 | Sanghvi et al. | 424/85.2 |

(Continued)

FOREIGN PATENT DOCUMENTS

WO  WO 2006/051542  5/2006

OTHER PUBLICATIONS

Kennedy, "High-intensity focused ultrasound in the treatment of solid tumors," *Nature Reviews: Cancer*, vol. 5, Mar. 18, 2005, pp. 321-327.

(Continued)

*Primary Examiner* — Hien N Nguyen
(74) *Attorney, Agent, or Firm* — Nixon & Vanderhye P.C.

(57) ABSTRACT

Methods of treating a subject suffering from a disease or a disorder associated with hyperproliferating cells. The method includes non-invasively administering to the subject ultrasound at a low intensity in a dose effective to selectively prevent the growth of the hyperproliferating cells or to eliminate the hyperproliferating cells in the subject, while substantially not affecting the cell viability of normal cells of the subject. The low intensity is pre-determined to be lower than a cavitational threshold intensity for a selected frequency.

20 Claims, 4 Drawing Sheets

(56) References Cited

U.S. PATENT DOCUMENTS

2011/0178441 A1* 7/2011 Tyler .................. A61N 7/00
  601/2
2013/0129799 A1* 5/2013 Shibaguchi .......... A61K 31/409
  424/400
2013/0131432 A1 5/2013 Kline

OTHER PUBLICATIONS http://physicaltherapyweb.com/therapeutic-ultrasound, retrieved Nov. 7, 2016.
Healing sound: the use of ultrasound in drug delivery and other therapeutic applications, by Samir Mitragotri, published in Nature Reviews—Drug Discovery, vol. 4, Mar. 2005, pp. 255-260.
Sponer, "Dependence of the Cavitation Threshold on the Ultrasonic Frequency," *Czech J. Phys.*, vol. 40: 1123-1132 (1990).
Kenneth S. Suslick: *Ultrasonic—Its chemical, physical and biological Effects*. NY VCH publications, pp. 20 and 311, 1988.

\* cited by examiner

LOW INTENSITY ULTRASOUND THERAPY

CROSS-REFERENCE TO RELATED APPLICATION(S)

This application is based upon and claims the benefit of U.S. Provisional Patent Application No. 61/773,169, filed on Mar. 6, 2013. The entire contents of which are incorporated herein by reference.

FIELD OF THE INVENTION

The present disclosure relates generally to the field of treatment of hyperproliferative diseases and disorders. More specifically, methods of treating a subject afflicted with cancer, neoplasms or metastatic cancer using ultrasound are disclosed.

BACKGROUND OF THE INVENTION

Ultrasound has been used for several decades in the medical field, mostly as a diagnostic tool, and to a lesser extent as a therapeutic device.

In most therapeutic methods ultrasound has been applied topically, either externally (on the skin surface) or internally (tympanal, buccal, vaginal or nasal applications). The common feature in this type of application is that the therapeutic effect results from increasing the penetration of the membrane, thereby enabling the delivery of medicines and/or other therapeutic agents. Another application of ultrasound which relies on enhancing the skin permeability is to increase the delivery out of the skin (namely for sensing purposes), thereby enhancing the sensitivity of measurement techniques (for example, measuring glucose levels on the skin). All of these methods require low intensity ultrasound, so that to avoid damaging the skin more than needed to increase its permeability, and have a short range of impact.

In some cases, ultrasonic therapy uses focused, localized heating to selectively destroy tissue anomalies. Heating a tissue beyond a critical temperature for a period of time causes necrosis, the destruction of tissue. Therefore, another type of therapeutic application of ultrasound is by using High Intensity Focused Ultrasound (HIFU), which is used to affect inner organs, mostly by ablation, without affecting the skin or intermediate membranes and/or tissues. Clinical HIFU procedures are typically performed in conjunction with an imaging procedure to enable treatment planning and targeting before applying a therapeutic or ablative levels of ultrasound energy. When Magnetic resonance imaging (MRI) is used for guidance, the technique is sometimes called Magnetic Resonance-guided Focused Ultrasound, often shortened to MRgFUS or MRgHIFU.

During the last decade many studies have concentrated on cancer treatment. Some of these studies focused on non-invasive, targeted treatment of cancerous cells by utilizing different triggers and drug carriers. Moreover, some applications, like ultrasound, have been tested for their ability to enhance drug release and carriers penetration into tumors. Other studies focused on identifying the effect of ultrasound on cancerous cells, albeit without comparing its effect on normal cells.

Specifically, ultrasound was used for cancer treatment in a number of methods which include: tumor exposure to ultrasound directly and indirectly (using HIFU) in order to increase drug or carrier/drug penetration into tumors, drug carriers exposure to ultrasound as a trigger for drug release and even tumor ablation by HIFU. For example, HIFU in the treatment of solid tumors is described by James E. Kennedy in *Nature Reviews Cancer*, published online 18 Mar. 2005, pages 321-327.

At high enough acoustic intensities both cavitation (abrupt microbubble formation as a result of liquid medium exposure to ultrasound) and temperature elevation can occur, which in turn, cause various kinds of tissue damage. Because the onset of cavitation and the resulting tissue damage can be unpredictable, it has generally been avoided in clinical applications. Furthermore, a disadvantage of methods relying on ablation and/or thermal elevation is that the tissue damage is not limited to the cancerous tissue, but unselectively affects all the neighboring healthy tissue within the treated area.

Several methods have been suggested to address this non-selectivity of ablation:

U.S. Pat. No. 7,481,781 disclosed the combined use of an electric field and ultrasound to ablate a cell or tissue.

PCT Publication No. WO 2006/051542 disclosed exposing nanoparticles to electromagnetic radiation under conditions wherein the nanoparticles generate microbubbles which emit heat when exposed to ultrasonic radiation.

US Patent Application No. 20130131432 disclosed a method to use Tuned resonant frequency ultrasound ("TRFU") at intensities as high as $10^7$ W/cm$^2$, for the treatment of cancer that selectively destroys neoplastic cells while leaving surrounding healthy tissue minimally affected. TRFU is based on the calculation of a resonant frequency according to the size of the cellular structure targeted for disruption. Namely, for certain types of cancerous cells, a resonance frequency is calculated, and the intensity is fitted accordingly, thereby reducing or eliminating the neoplastic cells. However, this method is "blind" to cancerous cells having the same size of normal cells, and furthermore the frequencies taught in this application are unconventionally high for therapeutic uses, and reach 16 MHz and higher.

However, none of the studies conducted so far have been able to provide a therapeutically non-invasive selective treatment method of cancer and/or other proliferative diseases, which will avoid causing damage to a healthy tissue, cells or organs, while being solely based on ultrasound at low intensities, as opposed to HIFU, which is also non-invasive, but uses high intensities of ultrasound, and avoided damage to tissues only by its focusing mechanism.

There is therefore a continuing need to find alternative therapeutically selective non-invasive treatment method of cancer and/or other proliferative diseases, which relies solely on ultrasound at low intensities.

BRIEF DESCRIPTION OF THE FIGURES

FIG. 3 shows NAR cell type average viability after exposure to ultrasound (20 kHz and 50% duty cycle) for different US intensities (1%, 3%, and 5% amplitudes or 4.15

W/cm², 4.38 W/cm² and 5.09 W/cm² respectively) and durations. P value<0.1 compared to control experiment;

DETAILED DESCRIPTION OF THE INVENTION

It has now been found by the inventors of the present invention that non-invasively exposing cancerous and metastatic cells to ultrasound at optimal low intensities results in higher mortality of cancerous cells and metastatic cells, as compared to normal and/or healthy cells. This enables the selective non-invasive treatment of cancer and other hyperproliferative diseases and disorders or tumors caused therefrom, without harming healthy tissue or cells, and while using solely ultrasound at low intensities.

Thus, according to one aspect of the invention, there is now provided a method of treating a subject suffering from a disease or a disorder associated with hyperproliferating cells, this method comprising non-invasively administering to the subject ultrasound at a low intensity, in a dose effective to prevent the growth of the hyperproliferating cells or to eliminate the hyperproliferating cells in the subject, while substantially not affecting normal cells of the subject.

Furthermore, the difference in selectivity of the present method implies that the cancerous cells do not need to be identified or marked in any way, since the method of the present invention will only affect the cancerous cells, and will not harm the healthy cells. Therefore, provided herein is a method utilizing the application of ultrasound at low intensities for the non-invasive treatment of hyperproliferative diseases and disorders or tumors caused therefrom, without combining it with other diagnostic tools or markers.

This is advantageous over, for example, the method disclosed in US Patent Application No. 20130131432 which will not be able to differentiate and/or affect a cancerous cell if it has the same size of a normal cell, at a given resonance frequency, and which used frequencies (16 MHz and higher) that may be considered exceptionally high in therapeutic applications of ultrasound.

As noted above, the method of the present invention can be based solely on the selectivity of the chosen ultrasound intensity, and does not need any additional methods or steps to identify or target the proliferative cells.

Thus, according to one preferred embodiment of the invention, the method provided herein avoids the use of any additional step for identifying or targeting the hyperproliferating cells.

As used herein, the term "treating" or "treatment", as is well understood in the art, refers to an approach for obtaining beneficial or desired results, including clinical results. These include, but are not limited to, curing, alleviation or amelioration of one or more symptoms or conditions, diminishment of extent of disease, stabilizing (i.e. not worsening) state of disease (e.g. maintaining a patient in remission), preventing spread of disease, delay or slowing of disease progression, amelioration or palliation of the disease state, diminishment of the reoccurrence of disease, and remission (whether partial or total), whether detectable or undetectable. The term "Treating" and "Treatment" can also mean prolonging survival as compared to expected survival if not receiving treatment. The term "treating" also includes inhibiting future onset or development of the disease.

As used herein, the term "subject" includes all members of the animal kingdom including mammals, and more preferably refers to humans. Optionally, the term "subject" includes mammals that have been diagnosed with cancer or are in remission.

As used herein, the term "disease" refers to any disease, disorder, condition or to any pathological or undesired condition, state, or syndrome, or to any physical, morphological or physiological abnormality.

As used herein, the term "disease or a disorder associated with hyperproliferating cells" used interchangeably with the term "hyperproliferative diseases and disorders", includes diseases which are associated with an abnormally proliferating cell population, and in particular diseases which are associated with an abnormally hyperproliferating cell population, such as tumors and/or cancers.

In accordance with another embodiment disclosed herein is a method of treating a subject suffering from a disease or a disorder associated with abnormal tissue growth comprising administering to the subject ultrasound at low intensity of up to 100 W/cm², and even as low as 12 W/cm², and over a period of time effective to inhibit or prevent the abnormal tissue growth in the subject.

In some embodiments of the method provided herein the subject is suffering from a tumor or a neoplasm. In various embodiments of the method provided herein the tumor is selected from a pre-malignant tumor and a malignant tumor. In some preferred embodiments of the method provided herein the abnormal tissue growth is malignant.

In another preferred embodiments of the method provided herein the disease or disorder is cancer. Preferably, the tumor is selected from the group consisting of a pre-malignant tumor and a malignant tumor.

In accordance with an embodiment provided herein is a method of treating a subject suffering from metastasis comprising administering to the subject ultrasound at a low intensity, in a dose effective to inhibit or prevent the growh and/or spread of metastasis in the subject.

The term "cancer" as used herein refers to a broad group of various diseases involving unregulated cell growth. In cancer, cells divide and grow uncontrollably, forming malignant tumors, and invade nearby parts of the body. The cancer may also spread to more distant parts of the body through the lymphatic system or bloodstream.

As used herein, the term "tumor" refers to a malignant tissue comprising transformed cells that grow uncontrollably. Non-limiting example of cancers and tumors include leukemias, lymphomas, myelomas, and the like; and solid tumors such as, for example, sarcomas and carcinomas, chordoma, endotheliosarcoma, lymphangiosarcoma, Ewing's tumor, brain tumor, skin tumor, breast tumor, colon carcinoma, pancreatic cancer, breast cancer, ovarian cancer, prostate cancer, Wilms' tumor, cervical cancer, testicular tumor, glioma, astrocytoma, medulloblastoma, craniopharyngioma, ependymoma, pinealoma, melanoma, neuroblastoma, and retinoblastoma.

Some Examples of tumors and/or cancers include, but are not limited to, metastatic cancers, cancers of the colon, uterine cervix, breast, pancreas, liver, lung, brain, retinoblastoma, skin (e.g., melanoma) or epidermal [e.g., squamous-cell carcinoma (SCC), basal cell carcinoma (BCC) and a non-melanoma skin cancer (NMSC)], lymphoma (e.g., Burkitt's lymphoma, non-Hodgkin's lymphoma) as well as various leukemias such as acute lymphoblastic leukemia (ALL), acute myeloid leukemias (AML) and chronic myeloid leukemia (CML).

In certain embodiments, the term "metastatic tumor", used interchangeably with the term "metastatic cancer", refers to a tumor that is capable of metastasizing, but has not yet metastasized to tissues or organs elsewhere in the body. In certain embodiments, the term metastatic tumor refers to a tumor that has metastasized to tissues or organs elsewhere in the body. In certain embodiments, metastatic tumors are comprised of metastatic tumor cells.

Thus, according to one preferred embodiment of the invention, the disease or the disorder is cancer, more preferably a metastatic cancer.

Other diseases with hyperproliferating cell population which can be treated by the method of the present invention include, but are not limited to, skin disorders, inflammatory proliferative disorders such as autoimmune proliferative disorders [e.g., rheumatoid arthritis (proliferative synovitis) and viral (e.g., EBV)—induced lymphoid proliferation], psoriasis, proliferative retinitis and ulcerative colitis and the like.

According to one preferred embodiment of the invention, the hyperproliferating cells are selected from the group comprising of cancerous and/or malignant and/or metastatic cells, or any combination thereof.

The term "cancerous cell" refers to a cell that exhibits one or more characteristics or hallmarks of cancer. Such hallmarks of cancer include self-sufficiency in growth signals, insensitivity to growth-inhibitory (antigrowth) signals, evasion of programmed cell death (apoptosis), limitless replicative potential, sustained angiogenesis, and tissue invasion and metastasis.

The term "malignant cell", as used herein, refers to a neoplastic or transformed cell.

The terms "neoplastic" refers to an abnormal mass of tissue as a result of neoplasia. Neoplasia is the abnormal proliferation NOF cells. The growth of neoplastic cells exceeds and is not coordinated with that of the normal tissues around it. The growth persists in the same excessive manner even after cessation of the stimuli. Neoplasms may be pre-cancerous or cancerous. In one embodiment, compositions and methods described herein are directed to pre-cancerous or cancerous cells. As used herein the term "Pre-cancerous" refers to an early form of cancer that is defined by the absence of invasion of tumor cells into the surrounding tissue. Pre-cancerous also refers to dysplasia, which is the earliest form of pre-cancerous lesion recognizable in a biopsy by a pathologist.

As used herein, the term "metastatic cell" as used herein is defined as the transfer of cancer cells from one organ or part to another organ or part which is not directly connected with it.

As used herein the term "administering" refers to ultrasonic stimulation of a cell, a tissue or an organ.

In the field of ultrasound treatment, ultrasound at intensities higher than a threshold intensity (depending on the various parameters such as tissue type, coupling medium properties, frequency, organ/tissue temperature and gas content) often cause some form of cavitation and temperature elevation, which in turn, causes various kinds of tissue damage not only to the cancerous tissue, but also to all of the neighboring exposed healthy tissue. Therefore the term "threshold intensity" is often referred to as "cavitational threshold intensity".

In contrast, as shown in the Examples below, the inventors have now shown that using ultrasound intensities lower than the cavitational threshold intensity, for example of 12 $W/cm^2$ and below, can be sufficient to selectively affect the viability of cancerous or malignant cells, as opposed to healthy and/or normal cells.

As used herein, the term "normal cell" used interchangeably with the term "healthy cell" describes a cell which does not exhibit uncontrolled cell growth and the ability to metastasize. The term "normal cell", as used herein, also encompassed the terms "benign cell" and "non-malignant cell".

Thus, according to one preferred embodiment of the invention, there is now provided a method of treating a subject suffering from a disease or a disorder associated with hyperproliferating cells, the method comprising non-invasively administering to the subject ultrasound at a low intensity in a dose effective to selectively prevent the growth of the hyperproliferating cells or to eliminate the hyperproliferating cells in the subject, while substantially not affecting the cell viability of normal cells of the subject, wherein the low intensity is pre-determined to be lower than a cavitational threshold intensity for a selected frequency.

The ultrasound treatment regime, also referred to as an ultrasound dose or "dose", includes a series of ultrasound parameters, including, but not limited to, ultrasound frequency, ultrasound intensity, duty cycle, treatment time.

These specific ultrasound working parameters (ultrasound dose) vary and may depend on a variety of factors, including the age, body weight, general health and sex of the individual being treated; other therapies and drugs that have been administered previously or in combination with the ultrasound therapy; and the type and severity of the particular condition (e.g. malignant disease) undergoing therapy.

Additional ultrasound working parameters include, but are not limited to, distance of transducer, area of transducer and additional parameters as detailed below, and as are known to a person skilled in the art.

While the exact intensity is determined by a person skilled in the art, according to all of these factors, the term "low intensity" refers to an intensity that is lower than the cavitational threshold intensity, and which selectively prevents the growth of the hyperproliferating cells or eliminates the hyperproliferating cells in the subject, while keeping normal cells substantially unaffected.

The terms "selectively prevent" and the term "substantially unaffected" as used herein, both refer to a selectivity in the effect of the ultrasound intensity on cell viability, between cancerous and non-cancerous cells.

According to one preferred embodiment, the method of the present invention results in a cell viability of less than 40% for hyperproliferating cells and, and a cell viability of more than 60% for normal cells.

According to another preferred embodiment, the method of the present invention results in a cell viability of less than 20% for hyperproliferating cells and a cell viability of more than 70% for normal cells.

Thus, cell viabilities of 60% or higher for normal cells, simultaneously reflect they are substantially unaffected by the method of the present invention.

This is quite in contrast to the use of HIFU on its own, which is just as harmful to normal tissue as it is to cancerous tissue. Hence, the selectivity of the HIFU method is restricted only by the focal area of the instrument, and not as a result of a different effect on healthy and cancerous cells/tissues, as in the present application. Therefore, while HIFU on its own cannot be used to treat cancer in sensitive or small areas, due to possible damage to adjacent tissues, its use in combination with the presently taught method can largely broaden the scope of use of HIFU and enable using it in treatments of cancer in areas that have not been treated by HIFU before and also be beneficial to larger tumors since it may speed the process and can be used more "freely" than in the current methods used today.

As noted hereinabove, the treatment regime includes, but is not limited to, intensity, frequency, duty cycle, time of the treatment, distance of transducer from the subject, and the area of the transducer.

Intensity

The term "ultrasound intensity" is used interchangeably with the terms "intensity", "power output", "power density", "power surface density", "acoustic output", and "spatial average intensity", measured in Watts per unit area, usually in Watt/cm$^2$ (W/cm$^2$) units.

While in HIFU applications, on its own, the ultrasound intensity is usually above 100 W (since HIFU is not relative to an area, the units are in watts) and even up to 10,000 W, the present invention shows that much lower intensities can be used, as long as they are lower than the cavitational threshold intensity, and are able to selectively differentiate between hyperproliferating cells and normal cells.

For example, for a frequency of 20 kHz, it was shown that the ultrasound intensities can be lower than 12 W/cm$^2$.

Thus, according to one embodiment of the invention, this method is characterized in applying the ultrasound at an intensity of up to 12 W/cm$^2$ at a frequency of 20 kHz.

It has also been shown that the ultrasound intensity can be as low as 10 W/cm$^2$, and even lower than 9 W/cm$^2$, and even lower than 6 W/cm$^2$; for example 4.15 W/cm$^2$, 4.38 W/cm$^2$ and 5.09 W/cm$^2$, while maintaining its selectivity on cell viability between cancerous and non-cancerous cells.

Thus, according to another preferred embodiment of the invention, the method is characterized in applying the ultrasound at an intensity of up to 6 W/cm$^2$.

It should be noted that these intensities were found to be effective for a frequency of 20 kHz, but for higher frequencies, such as up to 10 MHz, the intensity can be higher, for example until 100 W/cm$^2$. These intensities were found to be both lower than the cavitational threshold intensity, and be able to selectively differentiate between hyperproliferating cells and normal cells.

Therefore, according to another embodiment of the invention, this method is characterized in applying the ultrasound at an intensity of up to 100 W/cm$^2$ at a frequency of up to 10 MHz.

The process for finding the optimal ultrasound intensity, for a given ultrasound frequency, would generally proceed as follows: First, the cavitational threshold intensity should be determined for the specific application and conditions.

The term "cavitational threshold intensity" as used herein refers to the minimum intensity required to achieve the cavitation phenomenon. Namely, the minimum intensity at which the undesirable bubble formation occurs.

This value can be determined in a number of ways known to a person skilled in the art, and are most often determined by visual inspection of the cells, and determination of the intensity beyond which a visual collapse of cells and/or injury to an organ are determined.

Once the threshold intensity is determined it would serve as the maximal intensity to be tested for that frequency. As shown in the Examples section below, for both the in vitro and in vivo experiments, the intensity was easily set below the cavitational threshold intensity.

Then, approximately a tenth of the determined cavitational threshold intensity would be assessed for its effect on "healthy" and cancerous cells' viability. The intensity would be increased stepwise and the optimal intensity would be the one yielding the highest difference in cells viability of healthy and cancerous cells.

In the case of low frequencies, such as the 20 kHz frequency set in the Examples below, the stepwise increase in intensity may be difficult to demonstrate and adjust, and a higher flexibility in the setting of the intensity is achieved for higher frequencies.

Finally, as exemplified in Examples 1-3 below, the duration and duty cycle of the ultrasound application would be adjusted in order to control and fine tune the application to achieve maximal difference in the response of the hyperproliferative cells and the normal cells.

Thus, according to another preferred embodiment of the invention, there is provided a method of treating a subject suffering from a disease or a disorder associated with hyperproliferating cells, the method comprising non-invasively administering to the subject ultrasound at a low intensity, in a dose effective to selectively prevent the growth of the hyperproliferating cells or to eliminate the hyperproliferating cells in the subject, while substantially not affecting the cell viability of normal cells of the subject, wherein this intensity is pre-determined by:

a. Determining the cavitational threshold intensity for a selected frequency, thereby setting a maximal intensity for the frequency;
b. Setting an intensity of a tenth of the maximal intensity and measuring its effect on the cell viability of both normal cells and hyperproliferating cells;
c. Stepwise increasing the intensity to obtain an optimal intensity exhibiting the highest difference in cell viability between the normal cells and the hyperproliferating cells; and
d. Determining the duration and duty cycle of the ultrasound application to achieve the highest difference in cell viability between the normal cells and the hyperproliferating cells.

Since cavitational threshold intensity increases with ultrasound frequency, the higher the ultrasound frequency, the higher the ultrasound intensities that could be used, thus enabling greater differentiation between the response of healthy and hyperproliferative cells to ultrasound exposure.

Intensity Versus Medium

It should be noted that ultrasound amplitude percentage represents the ultrasound intensity of the instrument. However, it does not necessarily represent the ultrasound intensity that the cells and/or tissue have been exposed to. In the results presented hereinbelow, when exposing the cells/tissue directly to the ultrasound transducer (as was done in the in vivo experiments, Example 3), the ultrasound amplitude percentage of 1 and 2% correlates with exposure intensities of 7.7, 8.2 W/cm$^2$ (respectively). However, in the in vitro experiments (cell lines, Examples 1 and 2), ultrasound amplitude percentage of 1%, 2% and 3% correlate with exposure intensities of 4.15 W/cm$^2$, 4.3 W/cm$^2$ and 5.09 W/cm$^2$, respectively. The differences between the exposed intensities derive from the different manner by which the ultrasound was used in the in vitro experiments. Two main parameters affected the reduction in exposed intensity, the distance that the cells were from the transducer used (10 cm vs. 1-2 cm) and the probe size (13 cm vs 1.3 cm).

Frequency

The present invention is based on the selection of an optimal low intensity of ultrasound, at an intensity below the cavitational threshold intensity, that is selective in its effect on the viability of cancerous vs. normal cells, and can be used at virtually any frequency, quite in contrast to methods relying on high intensity of ultrasound, which are mainly based on high frequencies, and whereas there is no selective effect on cancerous cells.

As known to a person skilled in the art, the higher the frequency of the ultrasound, the more intensity that is needed to allow cavitation. Therefore, using low frequencies implies having a low threshold intensity for the formation of cavitation, and using higher frequencies provides a wider range of intensities before risking in the onset of cavitation.

According to one preferred embodiment, the frequency used in the present invention is a low frequency.

As used herein, the term "low frequency" or "LF" refers to frequencies ranging from 20 kHz-200 kHz.

According to another preferred embodiment, the frequency used in the present invention is a medium frequency.

As used herein, the term "medium frequency" or "MF" refers to frequencies ranging from 200 kHz to 1000 kHz (1 MHz).

According to another preferred embodiment, the frequency used in the present invention is a high frequency.

As used herein, the term "high frequency" or "HF" refers to frequencies higher than 1 MHz.

It should again be stressed that one advantage of the present invention is that it can be used at any ultrasound frequency, and is based on the selection of an optimal low intensity, as described hereinabove, which shows selectivity in the effect of the ultrasound treatment on cell viability, between cancerous and non-cancerous cells, while being lower than the cavitational threshold intensity.

The present invention preferably uses ultrasound frequencies ranging from 20 kHz to 10 MHz.

Duty Cycle

While in certain embodiments, the ultrasound can be administered continuously, in other embodiments, the ultrasound can be administered intermittently, using ON/OFF cycles. Those with skill in the art can determine effective ON/OFF cycle times depending, for example on the volume of tumor, type of tumor, and other relevant variables.

Another advantage of the methods and devices provided herein is that the hyperproliferative cells can be effectively treated in short periods of time.

In the case of using ON/OFF cycles, the term "duty cycle" is used to refer to the pulse duration divided by the pulse repetition period. In particular, duty cycle represents the fraction of time that the ultrasound is working, for example, 10% DC means that the ultrasound was on for 1 second and off for 9 seconds (for 1 minute duration, it means that ultrasound was on for 6 seconds and off for 54 seconds at ten seconds intervals).

According to one preferred embodiment of the present invention, the ultrasound is administered at a duty cycle ranging from 10% to 90%.

Additional Ultrasound Treatment Regime Parameters

Additional ultrasound treatment parameters include: time of application, distance of transducer from the skin of the subject (for non-HIFU applications), size and shape of the transducer, number of treatments, mode of application etc., and a person skilled in the art would easily determine these parameters, depending on the exact need and conditions.

The methods provided herein can be administered as a single treatment or as multiple courses of therapy. Those with skill in the art can determine whether several successive courses of treatment are required, based on the outcomes observed in the previous courses of therapy, until a particular criterion for terminating the patient's therapy is met.

According to one embodiment, the method described herein is characterized in applying the ultrasound at an application time ranging from 10 seconds to 10 minutes. This time refers to each separate treatment, and may be repeated as part of a treatment series. Preferably, the application time of each separate application is up to 1 minute, more preferably about 15 seconds.

The methods provided herein can be used as a monotherapy or in conjunction with other drugs such as, without being limited to, photosensitizers, sonosensitizers and chemotherapeutic agents; and or in conjunction with other therapies such as, without being limited to, anticancer radiotherapy. Such combinations may offer significant advantages, including synergistic activity, in therapy. In addition, such combinations may provide an improved quality of life compared to the quality of life the same patient would experience if they received only the chemotherapeutic agent as therapy. For example, the combined therapy with the low intensity ultrasound described herein may lower the dose of chemotherapeutic agents needed, thereby lessening the side-effects associated with high-dose chemotherapeutic agents (e.g., nausea, vomiting, hair loss, rash, decreased appetite, weight loss, etc.). The combination may also cause reduced tumor burden and the associated adverse events, such as pain, organ dysfunction, weight loss, etc.

In one preferred embodiment of the invention, the method provided herein is non-invasive. As used herein the term "non-invasive" refers to an external application, namely it comprises placing an ultrasonic transducer in contact with the surface of a patient's body or in close proximity to a patient's body, optionally through a coupling medium, that is used to facilitate transmission of the ultrasound energy from the machine head to the tissues.

The term "coupling medium" used in this context includes water, various oils, creams and gels. Ideally, the coupling medium should be relatively fluid so as to fill all available spaces yet relatively viscous so that it stays in place, have an impedance appropriate to the media it connects, and should allow transmission of ultrasound with minimal absorption, attenuation or disturbance. Preferably, the coupling medium is a gel.

Thus, according to one preferred embodiment, the method presented herein comprises placing an ultrasonic transducer in contact with the surface of the subject's body or in close proximity to the subject's body, optionally through a coupling medium. According to one preferred embodiment, in this case, the method described herein is characterized in applying the ultrasound at a transducer distance ranging from 0.5 cm to 5 cm from the subject. Preferably, the transducer distance is up to 4 cm from the subject.

While the person skilled in the art will easily determine the specific ultrasound treatment parameters, according to the exact need, in one preferred embodiment, the method described herein is characterized in applying regular ultrasound (non HIFU) at an intensity of up to 12 W/cm$^2$, a frequency of 20 kHz, a duty cycle ranging from 10% to 90%, at a time of up to 5 minutes, and at a transducer distance ranging from 0.5 cm to 4 cm from the subject.

However, the external non-invasive application of ultrasound also includes the application of High Intensity Focused Ultrasound, such as MRI-guided Focused Ultrasound or HIFU, which is external, yet affects internal organs.

Thus, in another preferred embodiment of the invention, the method provided herein is non-invasive and comprises applying a High Intensity Focused Ultrasonic transducer, optionally guided by an MRI system.

According to a most preferred embodiment, the method presented herein comprises applying a High Intensity Focused Ultrasonic transducer, guided by an MRI system.

Although the external non-invasive treatment is an advantage of the present invention, in another preferred embodiment of the invention, the method provided herein can be interventional and comprises inserting an ultrasonic transducer into a patient's body opening (such as esophagus, rectum, vagina).

Yet further, in certain embodiments the method provided herein can be used for treating hyperfroliferative cells ex vivo. These methods can be performed similar to other ex vivo methods, such as hemodialysis, for example. For example, in certain embodiments the method provided herein comprises extracting a physiological fluid (e.g., blood) from a subject suffering from a hyperproliferative disorder, for example blood cancer. After extraction, the physiological fluid is treated with ultrasound at low intensity such that the hyperproliferative cells have been sufficiently neutralized and/or prevented from growing and/or eliminated; and the treated physiological fluid is administered back to the subject.

Thus, according to one preferred embodiment, the method presented herein comprises applying ultrasound at a low intensity on a physiological fluid extracted from a subject suffering from a hyperproliferative disorder, followed by administering the physiological fluid back to the subject.

As noted hereinabove, one of the unique advantages of the method provided herein lies in the possibility of selectively destructing hyperprolifirating cells (e.g. cancerous cells) and/or tumors (e.g. metastatic cancer tumors) without the need to locate any or all of them. In addition, the method provided herein may be used in conjunction with or incorporated as part of, other treatments, such as for example chemotherapy treatment, to improve treatment effectiveness. Another important advantage of the method as described herein is that it may be applied as early as the cancer is detected, regardless of its stage.

Therefore, according to one preferred embodiment of the invention, the present method avoids the use of any additional step for identifying or targeting the hyperproliferating cells.

Furthermore, the method as disclosed herein can be used as preventive treatment for patients who overcome cancer, thereby preventing the cancer from recurring. Due to the ultrasound low intensities the method as provided herein is not expected to cause any undesirable side effects.

Therefore, according to another embodiment of the present invention, the methods disclosed herein are useful in treating a subject suffering from a disease or a disorder associated with nonmalignant or pre-malignant conditions, involving hyperproliferating cells and/or abnormal tissue growth.

The present disclosure is illustrated in detail below with reference to examples, but is not to be construed as being limited thereto.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Example 1

Effect of Ultrasound at Low Intensities on Cancerous Cell and Normal Cells

The effect of ultrasound at low intensities was tested on three cell lines: HeLa cells which are cancerous cells of ovarian cancer, NCI/ADR-RES (NAR) cells which are cancerous cells of ovarian cancer resistant to chemotherapy and MCF10A cells which are non-cancerous cells. The effects of intensity, duration and duty cycle of ultrasound on cells' mortality were evaluated.

Ultrasound transducer used for all of the experiments was with a frequency of 20 kHz (MISONIX, Model S-4000-010). Cell mortality was determined using a standard viability test using 3-(4,5-Dimethylthiazol-2-yl)-2,5-diphenyltetrazolium bromide (MTT) (available from Sigma, catalogue number M2128, CAS number: 298-93-1) that stains live cells only.

Cell Cultures

NAR cells were cultured in RPMI (Roswell Park Memorial Institute medium, Biological industries, 500 mL, Catalog: 01-109-1A) growth media containing 1% L-glutamine (Biological industries, 03-020-1B), 1% penicillin-streptomycin (Biological industries, Catalog number: 03-031-1B) and 10% fetal bovine serum (FBS, Biological industries, Catalog number: 04-121-1A) at 37° C. and 5% $CO_2$.

HeLa cells were cultured the same way as NAR cells except for using DMEM (Dulbecco's Modified Eagle's Medium, Biological industries 500 mL, Catalog: 01-055-1A) instead of RPMI.

MCF10A cells were cultured at 37° C. and 5% $CO_2$ with medium containing ingredients same as with HeLa cells and also: 1 mg/mL hydrocortisone suitable for cell culture (Sigma, Catalog number: H0888-1G), 10 mg/mL insulin from bovine pancreas powder (Sigma, catalog number: 16634-100 MG) with 1% acetic acid (FRUTAROM, Catalog: 5550030, and CAS no: 64-19-7), 1 mg/mL Cholera toxin *Vibrio cholera* (Sigma, Catalog number: C8052-0.5 MG), µg/mL 100 of EGF (Epidermal growth factor, Petro-Tech, E-Coli source, Catalog number: AF-100-15), 250 mL of F12 instead of FBS (Rhenium, Catalog number: 21765029) and 25 mL of US Donor Equine Serum (TAROM, catalog number: SH30074.03).

Figure 1:
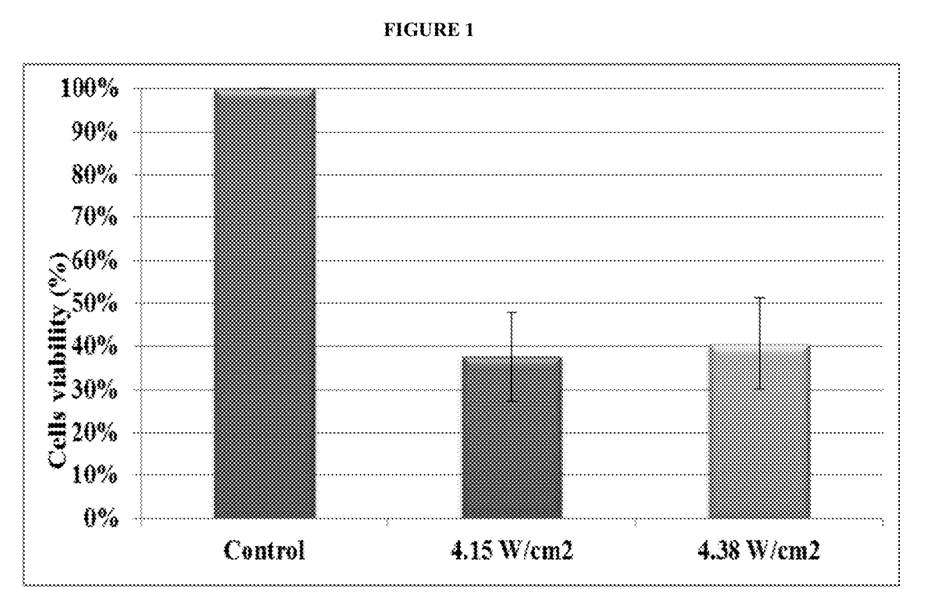
FIG. 1 shows HeLa cell type average viability after exposure to ultrasound (20 kHz and 50% duty cycle) for 1 minute at different intensities (1% and 3% amplitudes or 4.15 W/cm$^2$ and 4.38 W/cm$^2$, respectively). P value<0.1 compared to control experiment.

All of the results presented herein below represent an average and standard error of least three measurements. Initially, ultrasound intensities that would affect HeLa cells mortality were identified. Initial cells concentration before experiment was 160,000 cells/mL in all samples (determined by absorbance measurements, M-200 by TECAN, blank wavelength 670 nm reading subtracted from reading at 570 nm wavelength as described by Sigma procedure for MTT). FIG. 1 shows HeLa cell type average viability after exposure to ultrasound (20 kHz and 50% duty cycle) for 1 minute at different intensities (1% and 3% amplitudes). P value<0.1 compared to control experiment. In a control experiment cells were not exposed to ultrasound at any stage. FIG. 1 demonstrates that application of ultrasound (US) at the described parameters was below the cavitational threshold intensity, and caused about 60% mortality in HeLa cells.

The effect of low intensity ultrasound on mortality of cancerous cells was further evaluated in NAR cell type. In this experiment low intensity ultrasound effects on NAR cell type was compared to MCF10A cell type that is considered as "healthy" (non-cancerous) cell type. The effects of ultrasound duration and intensity on MCF10A cells and NAR cells viability are presented in FIGS. 2 and 3 (presented as average standard deviation of at least three experiments). US frequency and duty cycle (DC) were set on 20 kHz and 50% respectively.

Figure 2:
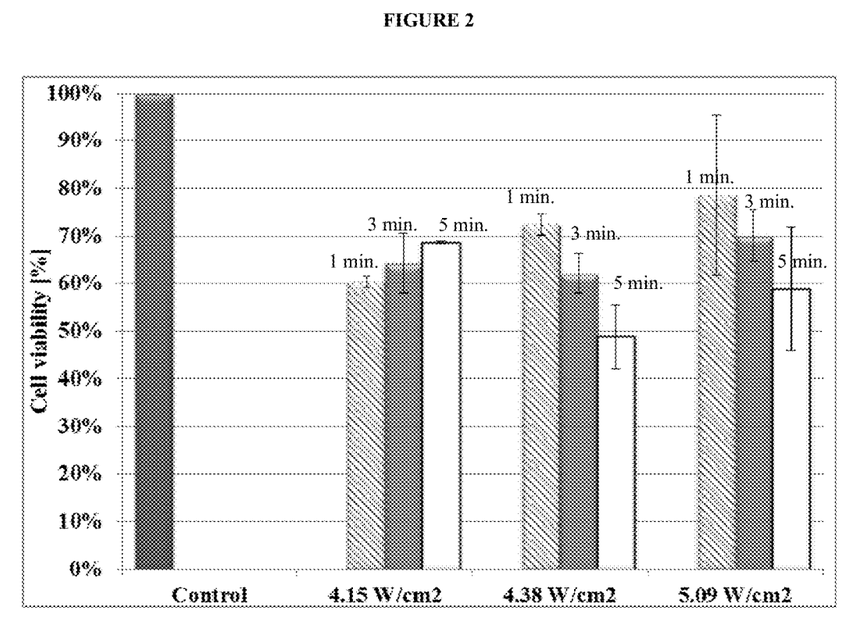
FIG. 2 shows MCF10A cell type average viability after exposure to ultrasound (20 kHz and 50% duty cycle) for different US intensities (1%, 3% and 5% amplitudes, or 4.15 W/cm$^2$, 4.38 W/cm$^2$ and 5.09 W/cm$^2$' respectively) and durations. P value<0.1 compared to control experiment.

FIG. 2 shows MCF10A cell type average viability after exposure to ultrasound (20 kHz and 50% duty cycle) for different ultrasound intensities and durations. P value<0.1 compared to control experiment.

Figure 3:
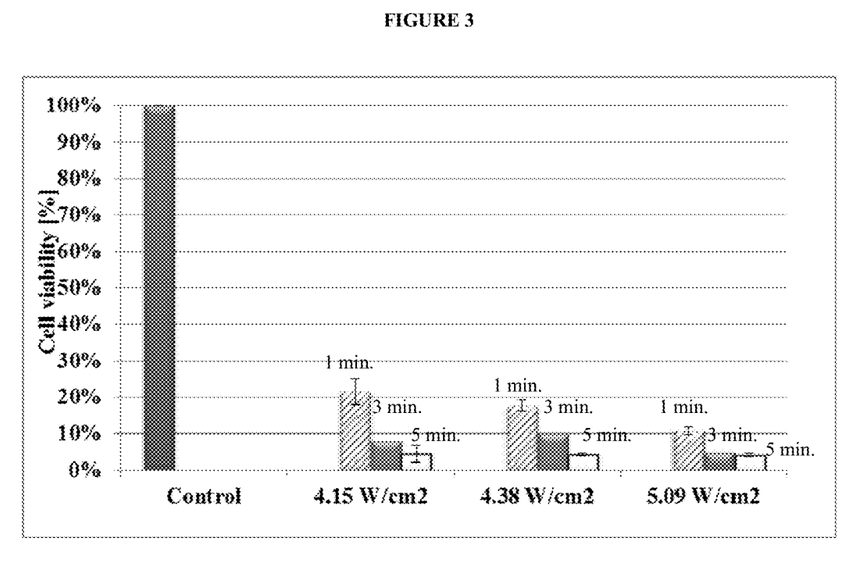

FIG. 3 shows NAR cell type average viability after exposure to ultrasound (20 kHz and 50% duty cycle) for different ultrasound intensities. P value<0.1 compared to control experiment.

The effect of ultrasound duration and intensity on MCF10A and NAR cell types viability can be observed in FIGS. 2 and 3. The control column represents cells, which were not exposed to ultrasound at any stage. Initial cells concentration was set to 160,000 cells/mL (determined by absorbance measurements, M-200 by TECAN, blank wavelength 670 nm reading subtracted from reading at 570 nm wave length as described by Sigma procedure for MTT). MCF10A cells were exposed to three different durations (1, 3 and 5 minutes) of ultrasound at two different intensities, while NAR cells were exposed to two different durations (1 and 5 minutes) of ultrasound at three different intensities. Fixed ultrasound parameters in all experiments were frequency of 20 kHz and 50% DC. These results demonstrate that application of ultrasound at the described parameters was below the cavitational threshold intensity.

The most dominant feature that can be observed from these figures is the fact that at any given ultrasound amplitude and duration, the mortality was higher for NAR cell type than MCF10A cell type, meaning that cancerous cells are much more sensitive to ultrasound exposure at low intensity. The average mortality of non-cancerous cells (MCF10A) was approximately 30% while the mortality of cancerous cells (NAR) was almost tripled and reaches approximately 80%.

The results also show that for MCF10A cells, mortality increased with the increase in duration of ultrasound exposure. Intensity wise, no trend was visible and also no statistical variance was found. This may be explained by the fact that the intensity was below the cavitational threshold intensity and that the increase in intensity was small (4.38 W/cm$^2$ and 5.09 W/cm$^2$ respectively). As for NAR cell type, at all amplitudes tested longer duration of ultrasound treatment resulted in higher NAR mortality. When ultrasound intensity was analyzed, a decrease in cell viability was observed with increase in US intensity, and as noted above all the intensities were below the cavitational threshold intensity.

To summarize, at all ultrasound intensities and exposure times tested, cancerous cells exhibited the highest mortality. NAR cells exhibited 80-95% mortality, HeLa cells exhibited 60-65% mortality (at 1 minute exposure only), while the mortality observed in non-cancerous cells (MCF10A) was 20-30%.

Example 2

Effect of Ultrasound Duty Cycle (DC) on Viability of Cancerous Cell and of Normal Cells This study was conducted utilizing the most extreme ultrasound conditions of 5 minutes exposure at 5% amplitude (equals 5.09 W/cm$^2$). This intensity was below the cavitational threshold intensity. Ultrasound frequency in this study was set to 20 kHz. In all previous experiments, duty cycle (DC) was set at 50% to avoid thermal effect. In this study 10% and 90% DC were also evaluated for their effect on NAR and MCF10A cell types. Cell cultures were prepared as described in Example 1.

Figure 4:
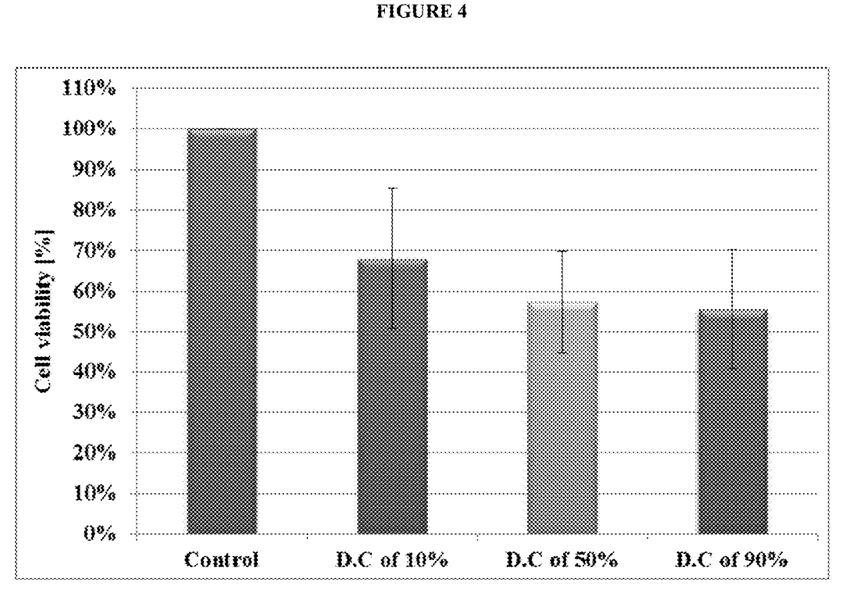
FIG. 4 shows MCF10A cell type average viability after 5 minutes exposure to ultrasound (20 kHz) at 5% amplitude (5.09 W/cm²) for different US duty cycles (10%, 50% and 90%). P value<0.1 compared to control experiment.
Figure 5:
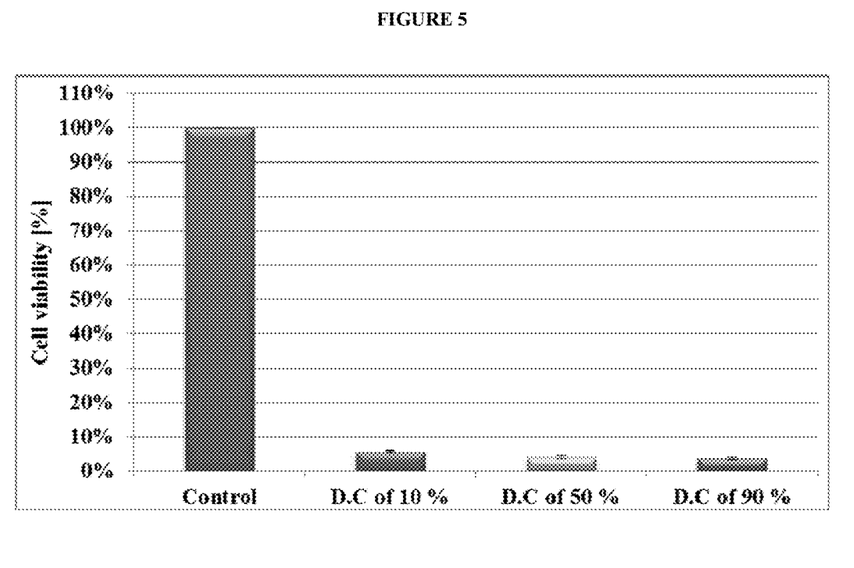
FIG. 5 shows NAR cell type average viability after 5 minutes exposure to ultrasound (20 kHz) at 5% amplitude (5.09 W/cm²) for different US duty cycles (10%, 50% and 90%). P value<0.1 compared to control experiment.

The effect of DC on cells viability can be observed in FIGS. 4 and 5.

FIG. 4 shows MCF10A cell type average viability after 5 minutes exposure to ultrasound (20 kHz) at 5% amplitude for different US duty cycles (10%, 50% and 90%). (P value<0.1 compared to control experiment.)

FIG. 5 shows NAR cell type average viability after 5 minutes exposure to ultrasound (20 kHz) at 5% amplitude for different US duty cycles (10%, 50% and 90%). (P value<0.1 compared to control experiment.)

FIGS. 4 and 5 indicate that both non-cancerous and cancerous cells were affected by ultrasound duty cycle. For both cell types, mortality increased with increased DC. In non-cancerous cells (MCF10A) mortality increased from 32% to 45% for 10% and 90% DC respectively, while in cancerous cells (NAR) the difference was much smaller, mortality increased from 94% to 96% for 10% and 90% DC respectively. This may suggest that mortality of cancerous cells at the ultrasound parameters that were used in this study, was already reaching the highest possible level, thus minimizing the effect.

The results of this study suggest that ultrasound DC can be used to control/minimize possible damage to healthy cells.

Example 3

In-Vivo Study in BALB C/J Mice Bearing KHJJ Mouse Breast Adenocarcinoma

This study was carried out in BALB C/J white albino mice bearing KHJJ mouse breast adenocarcinoma. BALB C/J mice are infected by implantation under the skin of one of the mouse's thighs. A total of 18 mice were used, divided into three groups (6 mice per group, mixed genders). The three groups consisted of control group (group 1) and two groups assessing the effect of two different low intensity ultrasound protocols (groups 2 and 3). The second thigh (uninfected with cancer) in groups 2 and 3 serves as the reference organ. Group 1 was not being exposed to ultrasound at any stage. Group 2 and 3 were exposed to two different low intensity ultrasound protocols. Mice were anesthetized prior to ultrasound exposure with a formula containing Ketamine and Xylazine, administered in an amount depending on animal weight (Ketamine 75 mg/kg and Xylazine 5 mg/kg animal body weight).

The low intensity ultrasound protocols were determined by a preliminary experiments assessing which parameters (namely time, intensity and DC) do not induce injury to skin and internal organs (cavitational threshold intensity).

All mice in all groups were not being treated for about two weeks in order for the tumors to reach a desired initial volume (approximately 100 mm$^3$). After these two weeks, mice in groups 2 and 3 were exposed twice a week to predetermined low intensity ultrasound protocol on both thighs (with and without tumor). Each group was exposed to one protocol. The coupling medium for ultrasound exposures was an ultrasound gel (by MEDI-PHARM, England). The control group (group 1) was exposed to ultrasound gel for the same duration as groups 2 and 3 (without exposure to ultrasound). Body weights were measured three times a week and observational notes were taken for any changes in behavior or appearance.

Tumor volumes were measured using a caliper (to measure diameter of the tumor) three times a week (one day post ultrasound treatment) in order to assess the effect of ultrasound exposures on tumor's volume.

A proof-of-concept testing was done in laboratory mice with KHJJ tumor. The effect of US (20 kHz) exposure for 30 sec, 50% DC with two intensities (7.7 and 8.5 W/cm$^2$) on mice's tumor growth rate was assessed. US duration was reduced (compared to in vitro experiments) due to preliminary results showing mild damage to the skin, and the necessity to lower the intensity below the cavitational threshold intensity.

US was used in tandem with ultrasonic gel. In a control group, the mice were not insonated.

Blood was aspirated from mouse's tumor post mortem, allowing the fluid to clot at 37° C. for 2 hours, and was kept in a refrigerator for a further 2 hours to allow the clot to shrink, and was finally centrifuged at 7000 rpm for 5 minutes.

Figure 6:
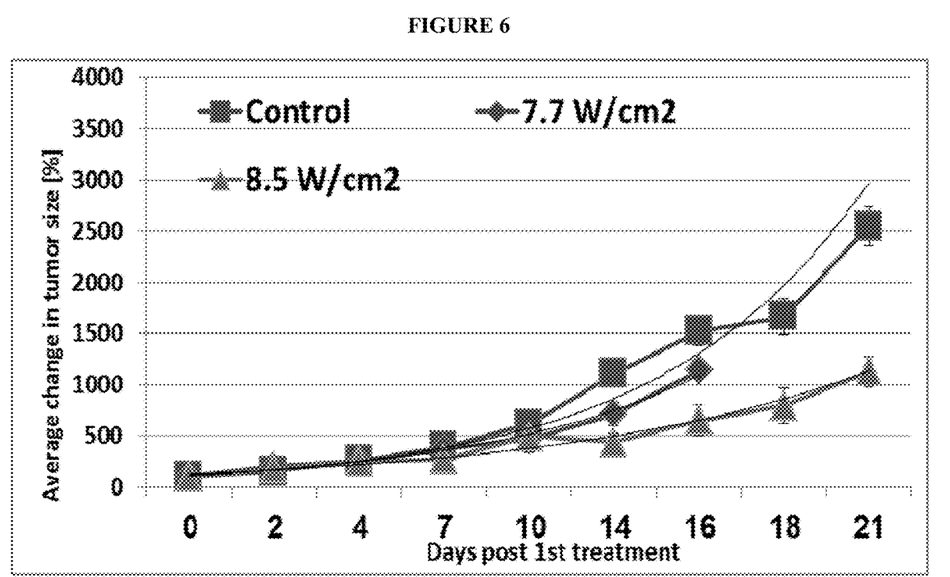
FIG. 6 shows the percentage of change in KHJJ tumor size in vivo (compared to tumor size pre first insonation) post US exposure (20 kHz and 50% DC) at two US intensities (7.7 and 8.5 W/cm²) and in a control group.

Exponential fit was assigned to each curve in FIG. 6. None of the treatments caused any visible damage to the insonated skin of both mice's flanks. The results shown in FIG. 6 show that the higher the US intensity used—the greater was the decrease in tumors growth rate (exponent value of 0.411>0.373>0.275 for control, 7.7 and 8.5 W/cm2 respectively). In addition, the tumor's stiffness was very different for insonated tumors compared to uninsonated. While the uninsonated tumors were quite rigid and whole, the insonated tumors were disintegrated and flaccid. Since large tumors develop necrotic cores and tumors were extracted when they reached a size of 1200 mm$^3$ or above, it was impossible to detect differences in histopathological samples of the tumors. However, the fluid that accumulated in the insonated tumors was tested and compared with blood of normal mice, and was found to differ greatly. This difference was further illustrated since the aspirated fluid from the tumor was not blood and it is assumed to be the content of cancerous exploded cells induced by the ultrasound exposure.

In summary, the in vivo experiment revealed two main features of insonating cancer tumors. The first feature is the reduced growth rate of the tumor as seen in FIG. 6 induced by insonation. The second feature is the disintegration of the cancer tumors as a result of cancerous cells explosion post insonation.

The invention claimed is:

1. A method of treating a subject suffering from a disease or a disorder associated with hyperproliferating cells, said method comprising non-invasively administering to said subject ultrasound in a dose effective to selectively prevent the growth of said hyperproliferating cells or to eliminate said hyperproliferating cells in said subject, while substantially not affecting the cell viability of normal cells of said subject, resulting in a cell viability of less than 40% of said hyperproliferating cells and a cell viability of more than 60% of said normal cells, wherein said ultrasound is administered at a transducer frequency ranging from 20 kHz -200 kHz and a transducer intensity of between 4 W/cm$^2$ and 100 W/cm$^2$, wherein said intensity is pre-determined such that said intensity is lower than a cavitational threshold intensity for the selected frequency.

2. The method of claim 1, wherein said ultrasound is at an intensity of between 4 W/cm$^2$ to 12 W/cm$^2$ and at a frequency of 20 kHz.

3. The method of claim 2, wherein said ultrasound is at an intensity of between 4 W/cm$^2$ to 6 W/cm$^2$.

4. The method of claim 1, wherein said hyperproliferating cells are selected from the group comprising cancerous cells, malignant cells and metastatic cells, or any combination thereof.

5. The method of claim 1, wherein said disease or said disorder is associated with abnormal tissue growth.

6. The method of claim 5, wherein said abnormal tissue growth comprises a tumor or a neoplasm.

7. The method of claim 6, wherein said tumor is selected from the group consisting of a pre-malignant tumor and a malignant tumor.

8. The method of claim 6, wherein said abnormal tissue growth is malignant.

9. The method of claim 1, wherein said disease or said disorder is cancer.

10. The method of claim 9, wherein said cancer is a metastatic cancer.

11. The method of claim 1, for the preventive treatment for patients who overcome cancer, thereby preventing the cancer from recurring.

12. The method of claim 1, characterized in applying a duty cycle ranging from 10% to 90%.

13. The method of claim 1, characterized in applying said ultrasound for an application time ranging from 10 seconds to 10 minutes for each treatment.

14. The method of claim 1, resulting in a cell viability of less than 20% of said hyperproliferating cells and a cell viability of more than 70% for said normal cells.

15. The method of claim 1, wherein said method avoids the use of any additional step for identifying or targeting said hyperproliferating cells.

16. The method of claim 1, wherein said method comprises applying a High Intensity Focused Ultrasonic transducer, guided by an MRI system.

17. The method of claim 1, wherein said method comprises placing an ultrasonic transducer in contact with the surface of said subject's body or in close proximity to said subject's body, optionally through a coupling medium.

18. The method of claim 17, wherein said ultrasound is at an intensity of between 4 W/cm$^2$ to 6 W/cm$^2$ and at a frequency of 20 kHz, a duty cycle ranging from 10% to 90%, at a time of up to 10 minutes, and at a transducer distance ranging from 0.5 cm to 4 cm from said subject.

19. The method of claim 1, wherein said method comprises applying said ultrasound at a low intensity on a physiological fluid extracted from said subject, followed by administering said physiological fluid back to said subject.

20. The method of claim 1, wherein said ultrasound is administered continuously.

* * * * *